(12) United States Patent
Jin et al.

(10) Patent No.: US 6,955,907 B1
(45) Date of Patent: Oct. 18, 2005

(54) ALKALINE, PROTEASE VAPK SUITABLE FOR LAUNDRY DETERGENT, VAPK GENE, RECOMBINANT EXPRESSION VECTOR, AND TRANSFORMED MICROORGANISMS

(75) Inventors: Ghee Hong Jin, Inchon (KR); Hyoung Suk Kim, Inchon (KR); Hyune Mo Rho, Seoul (KR); Hyune Whan Lee, Seoul (KR)

(73) Assignee: Cheil Jedang Corporation, Seoul (KR)

( * ) Notice: Subject to any disclaimer, the term of this patent is extended or adjusted under 35 U.S.C. 154(b) by 0 days.

(21) Appl. No.: 09/958,338
(22) PCT Filed: Jan. 14, 2000
(86) PCT No.: PCT/KR00/00022

§ 371 (c)(1),
(2), (4) Date: Oct. 9, 2001

(87) PCT Pub. No.: WO00/61769
PCT Pub. Date: Oct. 19, 2000

(30) Foreign Application Priority Data

Apr. 9, 1999 (KR) ........................ 1999-12588

(51) Int. Cl.[7] ........................ C12P 21/06; C12N 9/00; C12N 9/52; C12N 1/20; C12N 15/00
(52) U.S. Cl. .............. 435/220; 435/4; 435/6; 435/69.1; 435/195; 435/219; 435/221; 435/229; 435/252.3; 435/320.1; 435/183; 536/23.2; 536/23.7; 510/114; 510/515

(58) Field of Search ............... 435/4, 6, 183, 435/195, 219, 220, 221–229, 252–3, 320.1, 69.1, 41, 243, 252.32, 252.33, 252.34, 212, 213; 536/23.2, 23.7; 510/114, 515

(56) References Cited

U.S. PATENT DOCUMENTS 5,336,611 A 8/1994 van Eekelen et al.
5,858,748 A 1/1999 Jones et al.

OTHER PUBLICATIONS

Kwon YT et al. Biotechnol. Lett., 1994, vol. 16(4):413–418.*
Kwon et al., Gene, vol. 152, No. 11, pp. 59–63 (1995).
Munro et al., Microbiology, vol. 141, Pt. 7, pp. 1731–1738 (1995).
Genbank Accesion No., U36429, Jan. 1996, Jang W.H. et al.

* cited by examiner

Primary Examiner—Manjunath N. Rao
(74) Attorney, Agent, or Firm—Birch, Stewart, Kolasch & Birch, LLP

(57) ABSTRACT

A novel alkaline protease VapK suitable for a laundry detergent is disclosed. The gene vapk coding for the protease VapK, the recombinant plasmids containing said gene, and the transformed V. metshnikovii KS1 (pSBCm) with said recombinant plasmid are also disclosed. In addition, a process for producing the protease VapK is disclosed.

5 Claims, 10 Drawing Sheets

```
             HindIII                                          HindIII
  1   AGC TTC TAA TAC GAC TCA CTA TAG GGA AAG CTT TGC TTT CGG TTT 46   TTT CTG CCG CTT GAC AGA TAT TTA TGC GAT TCA TAA TGG ATA AAT
                      -35
                                                    AccI
 91   AAT CAT TAT AAA TCG CCA TGA TGT AAA TCA AGT AGA CTA AAA AAC
              -10

136   GTA CAG TTT TTT TTA CTT AAT AGT CTA TCA ATA TCA TTA ATT TAA

181   CCA ATA GGT AAC AAT TCA GTA AAT AAA AGC AAA CAC ATT CAC CCA

226   GCT AAT AAT AGC TTT ATT AAT AAA CTA TAA AAC TGG CGA ATG GCT

271   GCC GTT GTA ATG ATC CTT GAT GAG TGG TAT TTG CCA CTA ACA TTT

Pre →    MboII       HincII        ScaI
316   TAC AAG GAT AAA AAA ATG TTG AAG AAA AAT GTC AAC CGT ACA GTA
  1       SD                Met Phe Lys Lys Asn Val Asn Arg Thr Val A - X - B ↓
361   CTG GCT GGG TTA TTG TTG CCA ACT TCA ATC TCA CTG GCA ATA GCA
 11   Leu Ala Gly Leu Leu Lue Pro Thr Ser Ile Ser Leu Ala Ile Ala Pro →
406   TCT CAG CTT AAG GAT CAA GAA GTA CCG AGT TTT ACC CCC TCT GTT
 26   Ser Gln Leu Lys Asp Gln Glu Val Pro Ser Phe Thr Pro Ser Val 451   GCT GTT GAA AAT CAT CAA ACA GAA CAA CGC TAT TTT GTT ACC TAC
 41   Ala Val Glu Asn His Gln Thr Glu Gln Arg Tyr Phe Val Thr Tyr
                                XhoI
                                AvaII
496   GTG CCT GGG GCA ACC AGC GGA CCA ATG CGG ATG AGT CAA AAC GGC
 56   Val Pro Gly Ala Thr Ser Gly Pro Met Arg Met Ser Gln Asn Gly 541   TTA ACA GAA ACA GAT TTC TCT CTG CAA AAA GCC GCC GAT ATA TTA
 71   Leu Thr Glu Thr Asp Phe Ser Leu Gln Lys Ala Ala Asp Ile Leu ScaI                                              AvaI
586   AGT ACT CAG CAA GTA ACG GTC ATC AAT CAC CTC GAG TCA TTA CAT
 86   Ser Thr Gln Gln Val Thr Val Ile Asn His Leu Glu Ser Leu His 631   ACT TCA GTG GTT AGA GTG ACG CCA ACT CAA GCC AAG CAA CTG CTC
101   Thr Ser Val Val Arg Val Thr Pro Thr Gln Ala Lys Gln Leu Leu
                                                SalI,HincII,AccI
```

FIG. 5a

```
 676 GAT AAT GCT GAT GTG GCG ATG ATC GAA GTC GAC CCA ATA CGC TAT
 116 Asp Asn Ala Asp Val Ala Met Ile Glu Val Asp Pro Ile Arg Tyr

Mature →
 721 TTA TTC GAT GCT GAG ATT GAG CCT TAC GCA CAA CAG ACC CCA TAC
 131 Leu Phe Asp Ala Glu Ile Glu Pro Tyr Ala Gln Gln Thr Pro Tyr
                                         ============================

766 GGA ATC CGT ATG GTA CAA GCC GAT CAA CTC TCT GAC GTT TAT GCG
 146 Gly Ile Arg Met Val Gln Ala Asp Gln Leu Ser Asp Val Tyr Ala
                               *  AvaI   EcoRV
 811 GCT AAT CGT AAA GTT TGC GTC ATC GAC TCG GGA TAT CTT CGC AAC
 161 Ala Asn Arg Lys Val Cys Val Ile Asp Ser Gly Tyr Leu Arg Asn

856 CAT GTT GAT CTA CCG AGC GCT GGA GTC ACA GGC AGC ACT TTC TCT
 176 His Val Asp Leu Pro Ser Ala Gly Val Thr Gly Ser Thr Phe Ser
                                                       *
 901 GGC CAT GGT TCA TGG TTC ACT GAT GGC AAT GGT CAT GGA ACT CAC
 191 Gly His Gly Ser Trp Phe Thr Asp Gly Asn Gly His Gly Thr His

946 GTT GCA GGG ACA ATT GTC GCA CTG GAT AAT AAT GTC GGA GTT GTT
 206 Val Ala Gly Thr Ile Val Ala Leu Asp Asn Asn Val Gly Val Val

991 GGG GTT CTA CCG TCT GGC TTA GTC GGC CTA CAC AAC GTA AAA ATC
 221 Gly Val Leu Pro Ser Gly Leu Val Gly Leu His Asn Val Lys Ile

1036 TTT AAC GAT TCC GGT GTC TGG ACT CGC GCT TCG GAT TTG ATT CAA
 236 Phe Asn Asp Ser Gly Val Trp Thr Arg Ala Ser Asp Leu Ile Gln

1081 GCT ATC CAA TCT TGT CAA AGT GCA GGC AGT CAT GTG GTA AAT ATG
 251 Ala Ile Gln Ser Cys Gln Ser Ala Gly Ser His Val Val Asn Met

1126 AGT TTA GGT GGT AGC CAA GGC AGT GTA ACC GAA CAA AAG CCA ATG
 266 Ser Leu Gly Gly Ser Gln Gly Ser Val Thr Glu Gln Lys Pro Met

1171 CGT AAC TTT TAC CAA CAA GGG ATG CTC TTA GTT GCA GCA GCA GGT
 281 Arg Asn Phe Tyr Gln Gln Gly Met Leu Leu Val Ala Ala Ala Gly

1216 AAC TCA GGA AAC AGC GGC TTC TCA TAC CCG GCG TCT TAT GAT GCA
 296 Asn Ser Gly Asn Ser Gly Phe Ser Tyr Pro Ala Ser Tyr Asp Ala
                                 HincII
1261 GTG GTC TCA GTT GCG GCG GTT AAC TCA AGT GGT AAT GTG GCT AAC
 311 Val Val Ser Val Ala Ala Val Asn Ser Ser Gly Asn Val Ala Asn
```

FIG. 5b

```
1306 TTC TCA CAG TTC AAT TCA CAA GTT GAA CTC TCG GCA CCA GGA GTT
 326 Phe Ser Gln Phe Asn Ser Gln Val Glu Leu Ser Ala Pro Gly Val

1351 GGG GTA CTA TCA ACC GGT AAT AAT GGC GGC TAC TTA AGC TAT AGC
 341 Gly Val Leu Ser Thr Gly Asn Asn Gly Gly Tyr Leu Ser Tyr Ser

1396 GGA ACC TCA ATG GCT TCA CCT CAC GTT GCA GGT GTC GCA GCG CTG
 356 Gly Thr Ser Met Ala Ser Pro His Val Ala Gly Val Ala Ala Leu
                                      SalI,HincII,AccI
1441 GTT TGG AGT CAC TTT CCA CAA TGT CGA CCA GAG CGA ATC CGT CAG
 371 Val Trp Ser His Phe Pro Gln Cys Arg Pro Glu Arg Ile Arg Gln 1486 TCA CTC AGT CAA ACG GCT CTC GAT CGT GGT GCC GCA GGT AGA GAT
 386 Ser Leu Ser Gln Thr Ala Leu Asp Arg Gly Ala Ala Gly Arg Asp 1531 AAT TTT TAC GGT TGG GGG ATA GTT CAA GCG AGA CGT GCC TAT AAC
 401 Asn Phe Tyr Gly Trp Gly Ile Val Gln Ala Arg Arg Ala Tyr Asn
                                                     SspI
1576 TGG TTA TCT CGC AAT GGC TGT TAA TTT CTA ATA TTG AGA ATA TGA
 416 Trp Leu Ser Arg Asn Gly Cys Stop

1621(ACA GGG TAC TGA GTA CCC TGT)TTG TTA TTT TCC AGA GAC AAA TCT

1666 AAC CGT CTA AAT TAA TTT GTT TAA TCA ATT CTT CTT GTA CAC GGT

1711 CTG CCT CAG ATA AGG GAA TTT GAC AGG TTC CAG CGG CAT GAT GAC

1756 CGC CGC CAC CAT ATT TGA GCA TTA ACG CAC CAA CAT TGG TTT TGG

1801 AAC TAC GAT CTT TC
```

FIG. 5c

```
            140                        160      169         180
             |                          |        *          |
VapK    AQQT--PYGIRMVQ-----ADQL-SDVY-AANRKVC-VIDS-GYLRNHVDLPSAGV
VapT    SETTPWGYFAVKADQLEDSQAGNQTICI----------IDS-GYDLAHNDLSGNRV
BAE       QTV-PWGINRVQAPIAQSRGFT----- GTGVRVAVLDT-GISN-HADL---RI
CAR       QTV-PYGIPLIKADKVQAQGFK----- GANVKVAVLDT-GIQASHPDL---NV 190            202     210                    230
             |              *       |                      |
VapK    TGSTFSGHGSWFTDGNG -- HGTHVAGTI-VALDNNV-GVVGVLPSGLVGLHNV
VapT    TGTNDRG-TGQWYIPGSNNA-HGTHVAGTI-AAIANNE-GVKGLLPNQNVNLHIV
BAE     RGG-ASFVPGE--PNISDGNGHGTQVAGTI-AAL-NNSIGVLGVAPNVDLYG--V
CAR     VGG ASFVAGE--AYNTDGNGHGTHVAGTV-AALDNTT-GVLGVAPSVSLYA--V

240·                    260                  280
             |                       |                    |
VapK    KIFNDSGVWTRAS DLIQ-AIQSCQSAGSH--VVNMSLGGSQGSVTEQKPMRNF
VapT    KVFNESGWGYS-S TLVRAI-QTCADNGAKI--VNMSLGGSQSSRTEQNAMDAL
BAE     KVLGASGS--SIS-GIA-QGL-QWAANNGMHI--ANMSLGSSAGSATMEQAVNQA
CAR     KVLNSSGSG-TYS-GIVS-GI-EWATTNGMDV--1NMSLGGPSGSTAMKQAVDNA 290                 310
             |                   |
VapK    YQQGMLLYAAAAGNSG    NSGF-SYPASYDAVYS-VAAVMSSGHVANFSQFNS-
VapT    YERGVLMIAAAGNSG     NTAHS-YPASYDSVMS-VAAVDSNYDHASFSQATN-
BAE     TASGVLVVAASGNSGAG--NVGF---PARYANAMA-VGATDQNNWRATFS-----
CAR     YARGVVVVAAAGNSGSSG-NTNTIGYPAIYDSVIA-VGAVDSWSNRASFS-----

340            358               380
             |              *                 |
VapK    QVELSAPGVGVLSTGNNGGY-LSYSGTSHASPHVAGVAALVWSHFPQCRPERIRQ
VapT    QVEIAAPGVAVLSTVSVGEY-QYYNGTSHATPHYSGVAGLVWSYHPQCSAKQIRQ
BAE     ---------------Y-ASFNGTSHATPHVAGVAALVKQKNPSWSHVQIRN
CAR     ---------------Y-ATLNGTSHASPHVAGAAALILSKHPNLSASQVRN

422
                                          |
VapK    SLSQTALDRGAAGRDNFYGWGIVQARRAYNWLSRNGC
VapT    ALTQTALDLDVLARYIVLDG-IVTSWRKILTGQ
BAE     HLKNTATNLGNTTQFGSGLVNAEAATR
CAR     RLSSTATYLGSSFYYGKGLINVEAAAQ
```

FIG. 6

SEQUENCE LISTING

<160> NUMBER OF SEQ ID NOS: 6

<210> SEQ ID NO 1
<211> LENGTH: 422
<212> TYPE: PRT
<213> ORGANISM: Vibrio metschnikovii

<400> SEQUENCE: 1

```
Met Phe Lys Lys Asn Val Asn Arg Thr Val Leu Ala Gly Leu Leu Leu
1               5                   10                  15

Pro Thr Ser Ile Ser Leu Ala Ile Ala Ser Gln Leu Lys Asp Gln Glu
            20                  25                  30

Val Pro Ser Phe Thr Pro Ser Val Ala Val Glu Asn His Gln Thr Glu
        35                  40                  45

Gln Arg Tyr Phe Val Thr Tyr Val Pro Gly Ala Thr Ser Gly Pro Met
    50                  55                  60

Arg Met Ser Gln Asn Gly Leu Thr Glu Thr Asp Phe Ser Leu Gln Lys
65                  70                  75                  80

Ala Ala Asp Ile Leu Ser Thr Gln Gln Val Thr Val Ile Asn His Leu
                85                  90                  95

Glu Ser Leu His Thr Ser Val Val Arg Val Thr Pro Thr Gln Ala Lys
            100                 105                 110

Gln Leu Leu Asp Asn Ala Asp Val Ala Met Ile Glu Val Asp Pro Ile
        115                 120                 125

Arg Tyr Leu Phe Asp Ala Glu Ile Glu Pro Tyr Ala Gln Gln Thr Pro
    130                 135                 140

Tyr Gly Ile Arg Met Val Gln Ala Asp Gln Leu Ser Asp Val Tyr Ala
145                 150                 155                 160

Ala Asn Arg Lys Val Cys Val Ile Asp Ser Gly Tyr Leu Arg Asn His
                165                 170                 175

Val Asp Leu Pro Ser Ala Gly Val Thr Gly Ser Thr Phe Ser Gly His
            180                 185                 190

Gly Ser Trp Phe Thr Asp Gly Asn Gly His Gly Thr His Val Ala Gly
        195                 200                 205

Thr Ile Val Ala Leu Asp Asn Asn Val Gly Val Val Gly Val Leu Pro
    210                 215                 220

Ser Gly Leu Val Gly Leu His Asn Val Lys Ile Phe Asn Asp Ser Gly
225                 230                 235                 240

Val Trp Thr Arg Ala Ser Asp Leu Ile Gln Ala Ile Gln Ser Cys Gln
                245                 250                 255

Ser Ala Gly Ser His Val Val Asn Met Ser Leu Gly Gly Ser Gln Gly
            260                 265                 270

Ser Val Thr Glu Gln Lys Pro Met Arg Asn Phe Tyr Gln Gln Gly Met
        275                 280                 285

Leu Leu Val Ala Ala Gly Asn Ser Gly Asn Ser Gly Phe Ser Tyr
    290                 295                 300

Pro Ala Ser Tyr Asp Ala Val Val Ser Val Ala Ala Val Asn Ser Ser
305                 310                 315                 320

Gly Asn Val Ala Asn Phe Ser Gln Phe Asn Ser Gln Val Glu Leu Ser
```

-continued

```
                    325                 330                 335
    Ala Pro Gly Val Gly Val Leu Ser Thr Gly Asn Asn Gly Tyr Leu
                340                 345                 350

Ser Tyr Ser Gly Thr Ser Met Ala Ser Pro His Val Ala Gly Val Ala
                355                 360                 365

Ala Leu Val Trp Ser His Phe Pro Gln Cys Arg Pro Glu Arg Ile Arg
            370                 375                 380

Gln Ser Leu Ser Gln Thr Ala Leu Asp Arg Gly Ala Ala Gly Arg Asp
    385                 390                 395                 400

Asn Phe Tyr Gly Trp Gly Ile Val Gln Ala Arg Arg Ala Tyr Asn Trp
                    405                 410                 415

Leu Ser Arg Asn Gly Cys
                420
```

<210> SEQ ID NO 2
<211> LENGTH: 1813
<212> TYPE: DNA
<213> ORGANISM: Vibrio metschnikovii

<400> SEQUENCE: 2

| | | |
|---|---|---|
| agcttctaat acgactcact ataggaaag ctttgctttc ggtttttct gccgcttgac | 60 |
| agatattat gcgattcata atggataaat aatcattata aatcgccatg atgtaaatca | 120 |
| agtagactaa aaaacgtaca gttttttta cttaatagtc tatcaatatc attaatttaa | 180 |
| ccaataggta acaattcagt aaataaaagc aaacacattc acccagctaa taatagcttt | 240 |
| attaataaac tataaaactg gcgaatggct gccgttgtaa tgatccttga tgagtggtat | 300 |
| ttgccactaa cattttacaa ggataaaaaa atgttgaaga aaaatgtcaa ccgtacagta | 360 |
| ctggctgggt tattgttgcc aacttcaatc tcactggcaa tagcatctca gcttaaggat | 420 |
| caagaagtac cgagttttac cccctctgtt gctgttgaaa atcatcaaac agaacaacgc | 480 |
| tattttgtta cctacgtgcc tggggcaacc agcggaccaa tgcggatgag tcaaaacggc | 540 |
| ttaacagaaa cagatttctc tctgcaaaaa gccgccgata tattaagtac tcagcaagta | 600 |
| acggtcatca atcacctcga gtcattacat acttcagtgg ttagagtgac gccaactcaa | 660 |
| gccaagcaac tgctcgataa tgctgatgtg gcgatgatcg aagtcgaccc aatacgctat | 720 |
| ttattcgatg ctgagattga gccttacgca caacagaccc catacggaat ccgtatggta | 780 |
| caagccgatc aactctctga cgtttatgcg gctaatcgta aactttgcgt catcgactcg | 840 |
| ggatatcttc gcaaccatgt tgatctaccg agcgctggag tcacaggcag cactttctct | 900 |
| ggccatggtt catggttcac tgatggcaat ggtcatggaa ctcacgttgc agggacaatt | 960 |
| gtcgcactgg ataataatgt cggagttgtt ggggttctac cgtctggctt agtcggccta | 1020 |
| cacaacgtaa aaatctttaa cgattccggt gtctggactc gcgcttcgga tttgattcaa | 1080 |
| gctatccaat cttgtcaaag tgcaggcagt catgtggtaa atatgagttt aggtggtagc | 1140 |
| caaggcagtg taaccgaaca aaagccaatg cgtaactttt accaacaagg gatgctctta | 1200 |
| gttgcagcag caggtaactc aggaaacagc ggcttctcat acccggcgtc ttatgatgca | 1260 |
| gtggtctcag ttgcggcggt taactcaagt ggtaatgtgg ctaacttctc acagttcaat | 1320 |
| tcacaagttg aactctcggc accaggagtt ggggtactat caaccggtaa taatggcggc | 1380 |
| tacttaagct atagcggaac ctcaatggct tcacctcacg ttgcaggtgt cgcagcgctg | 1440 |
| gtttggagtc acttttccaca atgtcgacca gagcgaatcc gtcagtcact cagtcaaacg | 1500 |
| gctctcgatc gtggtgccgc aggtagagat aatttttacg gttgggggat agttcaagcg | 1560 |

```
agacgtgcct ataactggtt atctcgcaat ggctgttaat ttctaatatt gagaatatga  1620
acagggtact gagtaccctg tttgttattt tccagagaca aatctaaccg tctaaattaa  1680
tttgtttaat caattcttct tgtacacggt ctgcctcaga taagggaatt tgacaggttc  1740
cagcggcatg atgaccgccg ccaccatatt tgagcattaa cgcaccaaca ttggtttgga  1800
actacgatct ttc                                                    1813
```

```
<210> SEQ ID NO 3
<211> LENGTH: 283
<212> TYPE: PRT
<213> ORGANISM: Vibrio sp
<220> FEATURE:
<221> NAME/KEY: misc_feature
<222> LOCATION: (1)..(283)
<223> OTHER INFORMATION: VapK (Vibrio alkaline protease K)

<400> SEQUENCE: 3
```

```
Ala Gln Gln Thr Pro Tyr Gly Ile Arg Met Val Gln Ala Asp Gln Leu
1               5                   10                  15

Ser Asp Tyr Tyr Ala Ala Asn Arg Lys Val Cys Val Ile Asp Ser Gly
            20                  25                  30

Tyr Leu Arg Asn His Val Asp Leu Pro Ser Ala Gly Val Thr Gly Ser
        35                  40                  45

Thr Phe Ser Gly His Gly Ser Trp Phe Thr Asp Gly Asn Gly His Gly
    50                  55                  60

Thr His Val Ala Gly Thr Ile Val Ala Leu Asp Asn Asn Val Gly Val
65                  70                  75                  80

Val Gly Val Leu Pro Ser Gly Leu Val Gly Leu His Asn Val Lys Ile
                85                  90                  95

Phe Asn Asp Ser Gly Val Trp Thr Arg Ala Ser Asp Leu Ile Gln Ala
            100                 105                 110

Ile Gln Ser Cys Gln Ser Ala Gly Ser His Val Val Asn Met Ser Leu
        115                 120                 125

Gly Gly Ser Gln Gly Ser Val Thr Glu Gln Lys Pro Met Arg Asn Phe
    130                 135                 140

Tyr Gln Gln Gly Met Leu Leu Val Ala Ala Gly Asn Ser Gly Asn
145                 150                 155                 160

Ser Gly Phe Ser Tyr Pro Ala Ser Tyr Asp Ala Val Val Ser Val Ala
                165                 170                 175

Ala Val Asn Ser Ser Gly Asn Val Ala Asn Phe Ser Gln Phe Asn Ser
            180                 185                 190

Gln Val Glu Leu Ser Ala Pro Gly Val Gly Val Leu Ser Thr Gly Asn
        195                 200                 205

Asn Gly Gly Tyr Leu Ser Tyr Ser Gly Thr Ser Met Ala Ser Pro His
    210                 215                 220

Val Ala Gly Val Ala Ala Leu Val Trp Ser His Phe Pro Gln Cys Arg
225                 230                 235                 240

Pro Glu Arg Ile Arg Gln Ser Leu Ser Gln Thr Ala Leu Asp Arg Gly
                245                 250                 255

Ala Ala Gly Arg Asp Asn Phe Tyr Gly Trp Gly Ile Val Gln Ala Arg
            260                 265                 270

Arg Ala Tyr Asn Trp Leu Ser Arg Asn Gly Cys
        275                 280
```

```
<210> SEQ ID NO 4
```

```
<211> LENGTH: 279
<212> TYPE: PRT
<213> ORGANISM: Vibrio sp
<220> FEATURE:
<221> NAME/KEY: misc_feature
<222> LOCATION: (1)..(279)
<223> OTHER INFORMATION: VapT (Vibrio alkaline protease T)

<400> SEQUENCE: 4
```

Ser Glu Thr Thr Pro Trp Gly Tyr Phe Ala Val Lys Ala Asp Gln Leu
1               5                   10                  15

Glu Asp Ser Gln Ala Gly Asn Gln Thr Ile Cys Ile Ile Asp Ser Gly
            20                  25                  30

Tyr Asp Leu Ala His Asn Asp Leu Ser Gly Asn Arg Val Thr Gly Thr
        35                  40                  45

Asn Asp Arg Gly Thr Gly Gln Trp Tyr Ile Pro Gly Ser Asn Asn Ala
    50                  55                  60

His Gly Thr His Val Ala Gly Thr Ile Ala Ala Ile Ala Asn Asn Glu
65                  70                  75                  80

Gly Val Lys Gly Leu Leu Pro Asn Gln Asn Val Asn Leu His Ile Val
                85                  90                  95

Lys Val Phe Asn Glu Ser Gly Trp Gly Tyr Ser Ser Thr Leu Val Arg
            100                 105                 110

Ala Ile Gln Thr Cys Ala Asp Asn Gly Ala Lys Ile Val Asn Met Ser
        115                 120                 125

Leu Gly Gly Ser Gln Ser Ser Arg Thr Glu Gln Asn Ala Met Asp Ala
    130                 135                 140

Leu Tyr Glu Arg Gly Val Leu Met Ile Ala Ala Ala Gly Asn Ser Gly
145                 150                 155                 160

Asn Thr Ala His Ser Tyr Pro Ala Ser Tyr Asp Ser Val Met Ser Val
                165                 170                 175

Ala Ala Val Asp Ser Asn Tyr Asp His Ala Ser Phe Ser Gln Ala Thr
            180                 185                 190

Asn Gln Val Glu Ile Ala Ala Pro Gly Val Ala Val Leu Ser Thr Val
        195                 200                 205

Ser Val Gly Glu Tyr Gln Tyr Tyr Asn Gly Thr Ser Met Ala Thr Pro
    210                 215                 220

His Val Ser Gly Val Ala Gly Leu Val Trp Ser Tyr His Pro Gln Cys
225                 230                 235                 240

Ser Ala Lys Gln Ile Arg Gln Ala Leu Thr Gln Thr Ala Leu Asp Leu
                245                 250                 255

Asp Val Leu Ala Arg Tyr Ile Val Leu Asp Gly Ile Val Thr Ser Trp
            260                 265                 270

Arg Lys Ile Leu Thr Gly Gln
        275

```
<210> SEQ ID NO 5
<211> LENGTH: 244
<212> TYPE: PRT
<213> ORGANISM: Bacillus sp
<220> FEATURE:
<221> NAME/KEY: misc_feature
<222> LOCATION: (1)..(244)
<223> OTHER INFORMATION: BAE (Bacillus sp. elastase TaB)

<400> SEQUENCE: 5
```

Gln Thr Val Pro Trp Gly Ile Asn Arg Val Gln Ala Pro Ile Ala Gln
1               5                   10                  15

-continued

```
Ser Arg Gly Phe Thr Gly Thr Gly Val Arg Val Ala Val Leu Asp Thr
            20                  25                  30

Gly Ile Ser Asn His Ala Asp Leu Arg Ile Arg Gly Gly Ala Ser Phe
        35                  40                  45

Val Pro Gly Glu Pro Asn Ile Ser Asp Gly Asn Gly His Gly Thr Gln
 50                  55                  60

Val Ala Gly Thr Ile Ala Ala Leu Asn Asn Ser Ile Gly Val Leu Gly
 65                  70                  75                  80

Val Ala Pro Asn Val Asp Leu Tyr Gly Val Lys Val Leu Gly Ala Ser
                 85                  90                  95

Gly Ser Ser Ile Ser Gly Ile Ala Gln Gly Leu Gln Trp Ala Ala Asn
                100                 105                 110

Asn Gly Met His Ile Ala Asn Met Ser Leu Gly Ser Ser Ala Gly Ser
            115                 120                 125

Ala Thr Met Glu Gln Ala Val Asn Gln Ala Thr Ala Ser Gly Val Leu
130                 135                 140

Val Val Ala Ala Ser Gly Asn Ser Gly Ala Gly Asn Val Gly Phe Pro
145                 150                 155                 160

Ala Arg Tyr Ala Asn Ala Met Ala Val Gly Ala Thr Asp Gln Asn Asn
                165                 170                 175

Asn Arg Ala Thr Phe Ser Tyr Ala Ser Phe Asn Gly Thr Ser Met Ala
            180                 185                 190

Thr Pro His Val Ala Gly Val Ala Ala Leu Val Lys Gln Lys Asn Pro
            195                 200                 205

Ser Trp Ser Asn Val Gln Ile Arg Asn His Leu Lys Asn Thr Ala Thr
        210                 215                 220

Asn Leu Gly Asn Thr Thr Gln Phe Gly Ser Gly Leu Val Asn Ala Glu
225                 230                 235                 240

Ala Ala Thr Arg

<210> SEQ ID NO 6
<211> LENGTH: 250
<212> TYPE: PRT
<213> ORGANISM: Bacillus licheniformis
<220> FEATURE:
<221> NAME/KEY: misc_feature
<222> LOCATION: (1)..(250)
<223> OTHER INFORMATION: CAR (Bacillus licheniformis subtilisin
      Carlsberg)

<400> SEQUENCE: 6

Gln Thr Val Pro Tyr Gly Ile Pro Leu Ile Lys Ala Asp Lys Val Gln
1               5                  10                  15

Ala Gln Gly Phe Lys Gly Ala Asn Val Lys Val Ala Val Leu Asp Thr
            20                  25                  30

Gly Ile Gln Ala Ser His Pro Asp Leu Asn Val Gly Gly Ala Ser
        35                  40                  45

Phe Val Ala Gly Glu Ala Tyr Asn Thr Asp Gly Asn His Gly Thr
 50                  55                  60

His Val Ala Gly Thr Val Ala Ala Leu Asp Asn Thr Thr Gly Val Leu
 65                  70                  75                  80

Gly Val Ala Pro Ser Val Ser Leu Tyr Ala Val Lys Val Leu Asn Ser
                 85                  90                  95

Ser Gly Ser Gly Thr Tyr Ser Gly Ile Val Ser Gly Ile Glu Trp Ala
                100                 105                 110

Thr Thr Asn Gly Met Asp Val Ile Asn Met Ser Leu Gly Gly Pro Ser
```

|  |  |  |  |  |  |  |  |  |  |
|---|---|---|---|---|---|---|---|---|---|
| | | 115 | | | 120 | | | 125 | |
| Gly | Ser | Thr | Ala | Met | Lys | Gln | Ala | Val | Asp | Asn | Ala | Tyr | Ala | Arg | Gly |
| | 130 | | | | | 135 | | | | | 140 | | | | |
| Val | Val | Val | Val | Ala | Ala | Ala | Gly | Asn | Ser | Gly | Ser | Ser | Gly | Asn | Thr |
| 145 | | | | | 150 | | | | | 155 | | | | | 160 |
| Asn | Thr | Ile | Gly | Tyr | Pro | Ala | Lys | Tyr | Asp | Ser | Val | Ile | Ala | Val | Gly |
| | | | | 165 | | | | | 170 | | | | | 175 | |
| Ala | Val | Asp | Ser | Asn | Ser | Asn | Arg | Ala | Ser | Phe | Ser | Tyr | Ala | Thr | Leu |
| | | | 180 | | | | | 185 | | | | | 190 | | |
| Asn | Gly | Thr | Ser | Met | Ala | Ser | Pro | His | Val | Ala | Gly | Ala | Ala | Ala | Leu |
| | | 195 | | | | | 200 | | | | | 205 | | | |
| Ile | Leu | Ser | Lys | His | Pro | Asn | Leu | Ser | Ala | Ser | Gln | Val | Arg | Asn | Arg |
| | 210 | | | | | 215 | | | | | 220 | | | | |
| Leu | Ser | Ser | Thr | Ala | Thr | Tyr | Leu | Gly | Ser | Ser | Phe | Tyr | Tyr | Gly | Lys |
| 225 | | | | | 230 | | | | | 235 | | | | | 240 |
| Gly | Leu | Ile | Asn | Val | Glu | Ala | Ala | Ala | Gln | | | | | | |
| | | | | 245 | | | | | 250 | | | | | | |

ALKALINE, PROTEASE VAPK SUITABLE FOR LAUNDRY DETERGENT, VAPK GENE, RECOMBINANT EXPRESSION VECTOR, AND TRANSFORMED MICROORGANISMS

This application is the national phase under 35 U.S.C. § 371 of PCT International Application No. PCT/KR00/00022 which has an International filing date of Jan. 14, 2000, which designated the United States of America.

FIELD OF THE INVENTION

The present invention relates to an alkaline protease VapK suitable for a laundry detergent, produced by *Vibrio metschnikovii* KS1, and to the gene vapk coding for said protease.

Figure 1:
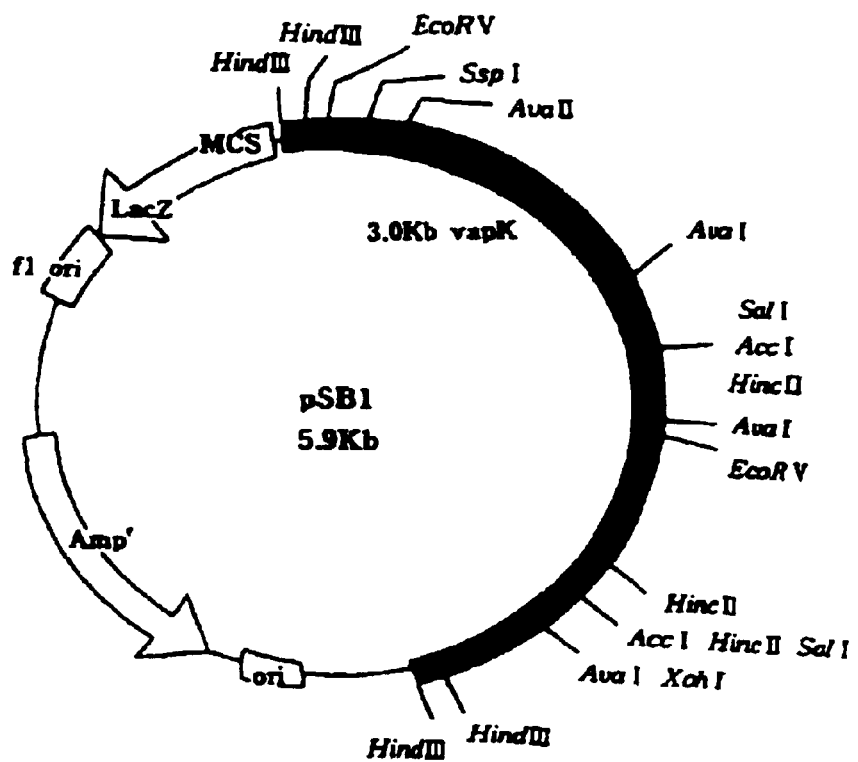
FIG. 1 shows the restriction map of the recombinant plasmid pSB1 of the present invention.

A: Agarose gel electrophoresis of plasmid pSB1 and *V. metschnikovii* KS1 chromosomal DNA digested by Hind III (lane 1: *V. metschnikovii* KS1 chromosomal DNA/Hind III; lane 2: *V. metshnikovii* KS1 chromosomal DNA; lane 3: pSB1 (super-coiled form); lane 4: pSB1/Hind III; lane 5: pT7T3/Hind III; lane 6: Pseudomonas sp. BK7; M: λDNA/Hind III)

B: Southern hybridization of DIG-labeled insert (0.7 kb) of pSB1 and *V metschnikovii* KS1 chromosomal DNA (lane 1: *V. metshnikovii* KS1 chromosomal DNA/Hind III; lane 2: *V. metshnikovii* KS1 chromosomal DNA; lane 3: pSB1 (super-coiled form); lane 4: pSB1/Hind III; lane 5: pT7T3/Hind III; lane 6: Pseudomonas sp. BK7; M: λ DNA/Hind III).

Figure 4:
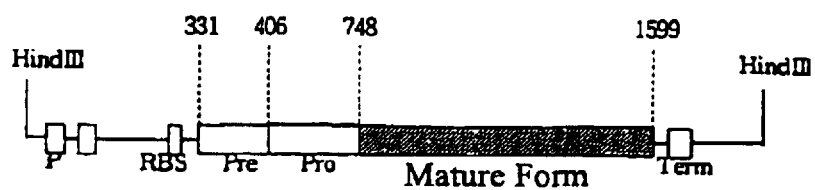

FIG. 4 illustrates the subcloning for identifying the minimum size of the vapk gene.

FIG. 5 shows the nucleotide sequence (SEQ ID NO:2) of the vapk gene and the deduced amino acid sequence (SEQ ID NO:1), wherein the symbol "=" indicates the mature form of N-terminal region identified by analysis of the N-terminal sequence and the symbol "*" indicates the active site.

FIG. 6 shows the comparison of the amino acid sequences of VapK (Vibrio alkaline protease K)(SEQ ID NO:3), VapT (Vibrio alkaline protease T)(SEQ ID NO:4), BAE (Bacillus sp. elastase TaB)(SEQ ID NO:5), and CAR (*Bacillus licheniformis* subtilisin Carlsberg)(SEQ ID NO:6), in which the symbol "*" indicates the active site.

Figure 7:
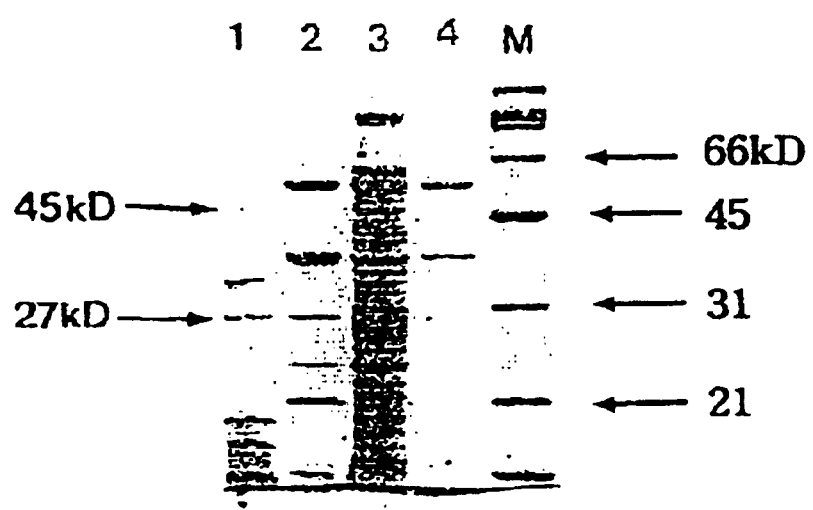

FIG. 7 shows the results of SDS-PAGE of the recombinant VapK expressed in *E. coli* [lane 1: *V. metschnikovii* culture broth; lanes 2 and 4: *E. coli* (pSB1) culture broth; lane 3: crude extract of *E. coli* (pSB1) culture cells; lane M: protein size markers indicating molecular weights].

Figure 8:
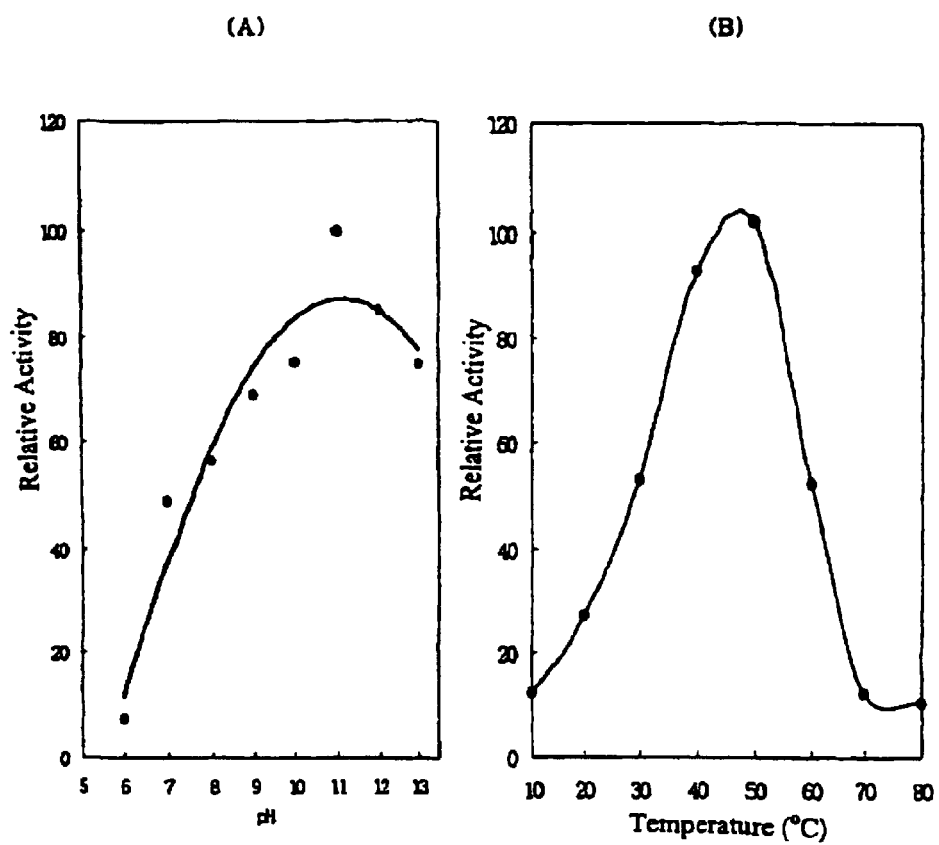

FIG. 8 shows the optimum pH and temperature of the recombinant VapK.

BACKGROUND OF THE INVENTION

Enzymes used as laundry detergents have been continually improved since their commercialization in the 1970s. To date, protease, lipase, amylase, and cellulase have been developed for laundry detergents. Among these, protease has been the most widely used as an additive of laundry detergent. Widely used alkaline protease for laundry detergents exhibit their optimal activity at pHs 8 to 12 and at temperature of 40° C. to 60° C. Most proteases used as detergent enzymes are produced by the Bacillus species. They are classified as a serine protease and are widely known as subtilisin.

Subtilisin exhibits stability in high temperature but is not stable under certain conditions. Specifically, its activity is not maintained for a prolonged period upon exposure to urea, a protein denaturizing agent. Subtilisin also quickly and irreversibly loses its proteolytic activity at pH 4 or below. Moreover, the activity of subtilisin is weak at low temperature (15° C. to 25° C.). As such, it cannot be used effectively in Southeast Asia and Central and South America where people usually wash with low temperature water.

U.S. Pat. Nos. 5,741,694 and 5,482,849 describe subtilisin with biochemical properties altered through a site-directed mutagenesis. U.S. Pat. No. 5,401,657 describes bacteria which produce an alkali-resistant enzyme useful as a laundry detergent.

We isolated a vapk gene encoding a protease enzyme VapK, which can be advantageously used in laundry detergent in that it remains active at high temperature and at high alkaline pH, and is resistant to many surfactants and protein denaturants widely used in laundry detergents. The gene vapk has been cloned, sequenced and brought to expression in useful host cell. The gene vapk consists of 1,266 bp coding for 422 amino acids, and the molecular weight of the protease VapK is 27 kda. This enzyme is very resistant to various surfactants such as AOS or LAS and exhibits optimum activity at pH 10.5 and at the temperature of 50° C. Moreover, the protease VapK is more active at low temperatures than are commercially availiable enzymes.

DETAILED DESCRIPTION OF THE INVENTION

The present invention provides a novel protease VapK having the following amino acid sequence (SEQ ID NO. 1):

```
Met Phe Lys Lys Asn Val Asn Arg Thr Val Leu Ala Gly Leu Leu Leu
1               5                   10                  15

Pro Thr Ser Ile Ser Leu Ala Ile Ala Ser Gln Leu Lys Asp Gln Glu
                20                  25                  30

Val Pro Ser Phe Thr Pro Ser Val Ala Val Glu Asn His Gln Thr Glu
            35                  40                  45

Gln Arg Tyr Phe Val Thr Tyr Val Pro Gly Ala Thr Ser Gly Pro Met
        50                  55                  60
```

-continued

```
Arg Met Ser Gln Asn Gly Leu Thr Glu Thr Asp Phe Ser Leu Gln Lys
 65                  70                  75                  80

Ala Ala Asp Ile Leu Ser Thr Gln Gln Val Thr Val Ile Asn His Leu
                 85                  90                  95

Glu Ser Leu His Thr Ser Val Val Arg Val Thr Pro Thr Gln Ala Lys
            100                 105                 110

Gln Leu Leu Asp Asn Ala Asp Val Ala Met Ile Glu Val Asp Pro Ile
        115                 120                 125

Arg Tyr Leu Phe Asp Ala Glu Ile Glu Pro Tyr Ala Gln Gln Thr Pro
    130                 135                 140

Tyr Gly Ile Arg Met Val Gln Ala Asp Gln Leu Ser Asp Val Tyr Ala
145                 150                 155                 160

Ala Asn Arg Lys Val Cys Val Ile Asp Ser Gly Tyr Leu Arg Asn His
                165                 170                 175

Val Asp Leu Pro Ser Ala Gly Val Thr Gly Ser Thr Phe Ser Gly His
            180                 185                 190

Gly Ser Trp Phe Thr Asp Gly Asn Gly His Gly Thr His Val Ala Gly
        195                 200                 205

Thr Ile Val Ala Leu Asp Asn Asn Val Gly Val Gly Val Leu Pro
    210                 215                 220

Ser Gly Leu Val Gly Leu His Asn Val Lys Ile Phe Asn Asp Ser Gly
225                 230                 235                 240

Val Trp Thr Arg Ala Ser Asp Leu Ile Gln Ala Ile Gln Ser Cys Gln
                245                 250                 255

Ser Ala Gly Ser His Val Val Asn Met Ser Leu Gly Gly Ser Gln Gly
            260                 265                 270

Ser Val Thr Glu Gln Lys Pro Met Arg Asn Phe Tyr Gln Gln Gly Met
        275                 280                 285

Leu Leu Val Ala Ala Ala Gly Asn Ser Gly Asn Ser Gly Phe Ser Tyr
    290                 295                 300

Pro Ala Ser Tyr Asp Ala Val Val Ser Val Ala Ala Val Asn Ser Ser
305                 310                 315                 320

Gly Asn Val Ala Asn Phe Ser Gln Phe Asn Ser Gln Val Glu Leu Ser
                325                 330                 335

Ala Pro Gly Val Gly Val Leu Ser Thr Gly Asn Asn Gly Gly Tyr Leu
            340                 345                 350

Ser Tyr Ser Gly Thr Ser Met Ala Ser Pro His Val Ala Gly Val Ala
        355                 360                 365

Ala Leu Val Trp Ser His Phe Pro Gln Cys Arg Pro Glu Arg Ile Arg
    370                 375                 380

Gln Ser Leu Ser Gln Thr Ala Leu Asp Arg Gly Ala Ala Gly Arg Asp
385                 390                 395                 400

Asn Phe Tyr Gly Trp Gly Ile Val Gln Ala Arg Arg Ala Tyr Asn Trp
                405                 410                 415

Leu Ser Arg Asn Gly Cys
            420
```

The present invention also provides a vapk gene having the following nucleotide sequence (SEQ ID NO. 2):

```
agcttctaat acgactcact atagggaaag ctttgctttc ggttttttct gccgcttgac    60
agatatttat gcgattcata atggataaat aatcattata aatcgccatg atgtaaatca   120
```

```
                              -continued
agtagactaa aaaacgtaca gtttttttta cttaatagtc tatcaatatc attaatttaa       180
ccaataggta acaattcagt aaataaaagc aaacacattc acccagctaa taatagcttt       240
attaataaac tataaaactg gcgaatggct gccgttgtaa tgatccttga tgagtggtat       300
ttgccactaa cattttacaa ggataaaaaa atgttgaaga aaaatgtcaa ccgtacagta       360
ctggctgggt tattgttgcc aacttcaatc tcactggcaa tagcatctca gcttaaggat       420
caagaagtac cgagttttac cccctctgtt gctgttgaaa atcatcaaac agaacaacgc       480
tattttgtta cctacgtgcc tggggcaacc agcggaccaa tgcggatgag tcaaaacggc       540
ttaacagaaa cagatttctc tctgcaaaaa gccgccgata tattaagtac tcagcaagta       600
acggtcatca atcacctcga gtcattacat acttcagtgg ttagagtgac gccaactcaa       660
gccaagcaac tgctcgataa tgctgatgtg gcgatgatcg aagtcgaccc aatacgctat       720
ttattcgatg ctgagattga gccttacgca aacagaccc catacggaat ccgtatggta       780
caagccgatc aactctctga cgtttatgcg gctaatcgta aactttgcgt catcgactcg       840
ggatatcttc gcaaccatgt tgatctaccg agcgctggag tcacaggcag cactttctct       900
ggccatggtt catggttcac tgatggcaat ggtcatggaa ctcacgttgc agggacaatt       960
gtcgcactgg ataataatgt cggagttgtt ggggttctac cgtctggctt agtcggccta      1020
cacaacgtaa aaatcttaa cgattccggt gtctggactc gcgcttcgga tttgattcaa      1080
gctatccaat cttgtcaaag tgcaggcagt catgtggtaa atatgagttt aggtggtagc      1140
caaggcagtg taaccgaaca aaagccaatg cgtaacttt accaacaagg gatgctctta      1200
gttgcagcag caggtaactc aggaaacagc ggcttctcat acccggcgtc ttatgatgca      1260
gtggtctcag ttgcggcggt taactcaagt ggtaatgtgg ctaacttctc acagttcaat      1320
tcacaagttg aactctcggc accaggagtt ggggtactat caaccggtaa taatggcggc      1380
tacttaagct atagcggaac ctcaatggct tcacctcacg ttgcaggtgt cgcagcgctg      1440
gtttggagtc actttccaca atgtcgacca gagcgaatcc gtcagtcact cagtcaaacg      1500
gctctcgatc gtggtgccgc aggtagagat aatttttacg gttggggat agttcaagcg      1560 agacgtgcct ataactggtt atctcgcaat ggctgttaat ttctaatatt gagaatatga      1620
acagggtact gagtaccctg tttgttattt tccagagaca aatctaaccg tctaaattaa      1680
tttgtttaat caattcttct tgtacacggt ctgcctcaga taagggaatt tgacaggttc      1740
cagcggcatg atgaccgccg ccaccatatt tgagcattaa cgcaccaaca ttggtttgga      1800
actacgatct ttc                                                        1813
```

In addition, the present invention provides a recombinant plasmid pSB1 containing the vapk gene and expressing it.

Further, the present invention provides a recombinant plasmid pSBCm containing the vapk gene and expressing it in a high yield.

Furthermore, the present invention provides a *Vibrio metschnikovii* KS1 (pSBCm) formed by transformation of *V. metschnikovii* KS1 with the recombinant plasmid pSBCm.

The present invention also provides a process for producing the protease VapK comprising the steps of culturing the *V. metschnikovii* KS1 (pSBCm) under conditions which allow the expression of protease VapK, and purifying it from the culture broth.

The characteristics of the recombinant plasmids pSB1 and pSBCm according to the present invention and the processes for producing said plasmids are described below.

Recombinant Plasmid pSB1 (FIG. 1)

For cloning the vapk gene, chromosomal DNA of *V. metschnikovii* KS1 was partially digested and inserted into a vector pT7T3 19U. The resulting recombinant vectors were introduced into a host cell. The transformed microorganisms were cultured on a solid agar medium containing skim milk and the transformant, showing a clear halo, was isolated. The plasmid was isolated and identified from the transformant. The identified plasmid was revealed that it contains a 3.0 kb DNA insert and two Hind III sites. The *E. coli* cells having the isolated plasmid DNA were cultured. The alkaline protease in the culture solution was analyzed and determined to have a molecular weight of 27 kDa and to exhibit optimum activity at pH 10.5.

Recombinant Plasmid pSBCm (FIG. 2)

The recombinant plasmid was transformed into *V. metschnikovii* KS1 to increase the productivity of the alkaline protease. Therefore, selection factors, such as antibiotic-resistance or colony-discoloration, were used to isolate the clone. The 3.0 kb vapk gene contained in plasmid pSB1 was subcloned into vector pKF3 which includes the cat-5 gene for chloramphenicol resistance (Cm). *V. metschnikovii* KS1 is sensitive to the antibiotic chloramphenicol. Therefore, it is easy to select the clone formed by transforming *V. metschnikovii* KS1 with the recombinant vector. The ampicilin-resisting factor is not suitable for the selection of the clone because *V. metschnikovii* KS1 shows resistance to the antibiotic ampicilin. The plasmid pSB1 was digested with Hind III and the resulting fragment was subcloned into the vector pKF3 digested with the same restriction enzyme Hind III. The recombinant vector obtained therefrom was introduced into *E. coli*. A strain exhibiting resistance to chloramphenicol and showing halo arround the colony on the skim-milk plate was isolated. The isolated strain contains the recombinant plasmid pSBCm. This pSBCm vector was used in transforming *V. metschnikovii* KS1.

In addition to *V. metschnikovii* KS1, *E. coli* HB101, *E. coli* JM101, *E. coli* Top10F', *V. metschnikovii* RH530 N4-8, etc. can be used as a host.

To produce the desired alkaline protease, the transformed *V. metschnikovii* KS 1 was cultured in an LSC medium consisting of 1% Bacto-tryptone, 0.5% yeast extract, 1% sodium chloride, and 100 mM sodium carbonate buffer solution, pH 10.5.

The activity of the alkaline protease was determined by the method of Yanagida et al with minor modifications. The reaction mixture was prepared by mixing 100 mM sodium carbonate solution with the supernatant formed after centrifuging the culture broth at 6,000 rpm for 15 minutes. 0.5 ml of the fermentation broth was mixed with 2.5 ml of 1% prewarmed casein solution in 100 mM sodium carbonate buffer (pH 10.5). The resulting mixture was incubated at 37° C. for 10 minutes. The reaction was terminated by adding a solution consisting 0.22 M trichloroacetic acid, 0.22 M sodium acetate and 0.22 M acetic acid. The reaction mixture was placed on ice for 10 minutes followed by centrifugation. 1 ml of the supernatant was mixed with 9 ml of distilled water. The optical density (O.D.) was measured at 280 nm. The result is indicated as unit. One unit of the enzyme is defined as the amount of protein which produces an increase of 0.1 absorbance unit under the assay conditions.

The gene sequencing was conducted by a dideoxy chain termination method (Sanger et al., 1997, Proc. Natl. Acad. Sci. USA. 74: 5463–5467).

The invention will now be described with reference to the following illustrative Examples.

EXAMPLES

Example 1

Construction of Recombinant Plasmid pSB1

The recombinant plasmid pSB1 was constructed by a shot-gun cloning method. After growth of *V. metschnikovii* KS1, an alkaline overproducing-mutant, its chromosomal DNA was separated by the Mamur method (Mamur, et al., J. Mol. Biol. 3:208–218, 1961). The chromosomal DNA was partially digested with Hind III, and the fragment was precipitated with ethanol and recovered. The plasmid pT7T3 19U was prepared by the Birnboim and Doly method (Nucleic acids Res. 7:1513–1523, 1979), and digested with Hind III. Both DNAs were ligated. The resulting recombinat plasmid was introduced into *E. coli* HB101. The transformant was plated on an LB-Ap-skim milk medium containing 1% bacto-tryptone, 0.5% bacto-yeast extract, 1% NaCl, 40 μg/ml of ampicilin, and 1% skim milk. Several colonies, each forming a clear halo around the colony, were selected as the clones possessing the alkaline protease gene. One of them was confirmed as harboring the vapk gene encoding the alkaline protease VapK. The recombinant plasmid with the vapk gene was designated as pSB1. The nucleotide sequence of the vapk gene of pSB1 and the amino acid sequence of the expressed alkaline protease VapK were determined. In addition, the properties of the alkaline protease VapK were studied.

Example 2

Identification of the Recombinant Plasmid pSB1

FIG. 1 shows the restriction map of the recombinant plasmid pSB1. The plasmid pSB1 is 5.9 kb in length and contains 3.0 kb vapk gene. A Southern blotting with the chromosomal DNA of *V. metschnikovii* KS1 was performed with the 3.0 kb vapk gene probe. As a result, it was concluded that the cloned gene was derived from *V. metschnicovii* KS1. In addition, the recombinant vapk gene was digested with various restriction enzymes including Bal 31 exonuclease. As a result, it was found that at least 2.1 kb of the vapk gene is required for encoding the alkaline protease VapK (FIG. 4).

Example 3

Illustration of the Nucleotide Sequence of the vapk Gene

The 3.0 kb vapk gene was digested with various restriction enzymes. Each of the resulting fragments was subcloned into plasmid pUC19. The overlapping sites were drawn. The nucleotide sequence was determined based on such overlapping sites (SEQ ID Nos 1 and 2, and FIG. 5). A single open reading frame (ORF) of 1,266 bp exists between base 331 and base 1,596. The real molecular weight of the protease VapK is 27 kDa as mentioned above. However, the MW of the enzyme deduced from the ORF is 45 kDa. The difference results from the processing of the precursor region during the extracellular secretion of the protease VapK.

The precursor region is the signal sequence inducing the extracellular secretion of the expressed protein and consists of 25 amino acids. The site between Ala 25 and Ser 26 is expected to be processed. The amino acid positions 3 and 4 which are highly basic amino acids are lysine. The amino acid positions 5 through 25 include strongly hydrophobic amino acids. The −35 region (5'TTGACA3'), −10 region (5'TATAAAT3') and Shine-Dalgarno (SD) sequence (5'CAAGGA3') located 8 bp upstream of the initiation codon (ATG) are similar to those previously reported (FIG. 5). The dyad symmetrical sequence, located 18 bp downstream of the stop codon TAA, forms a stem-loop structure and functions as a rho (ρ) independent terminator. The amino acid sequence of the protease VapK deduced from the nucleotide sequence of the vapk gene was compared to a variety of known proteases (FIGS. 6 and 7).

As shown in FIGS. 6 and 7, the protease VapK has 8%, 29%, and 29% nucleotide sequence homology with VapT, TaB, and Bacillus subtilisin Carlsberg, respectively. In addition, it is observed that His-202, Asp-169 and Ser-358 are well conserved as the active sites of all proteases (FIGS. 6 and 7).

Example 4

Characteristics of the Protease VapK Expressed from the Recombinant Plasmid pSB1

*E. coil* HB101 harboring the plasmid pSB1 was cultured in an LB medium. The culture broth was recovered and subjected to electrophoresis. As a result (FIG. 8), the expressed protease VapK was detected at the 27 kDa band. In addition, the proteolytic activity of the enzyme was measured. The results are shown in Table 1 below.

TABLE 1

The proteolytic activity of expressed Vap K

| Strain | Activity (unit/ml) |
|---|---|
| Vibrio metschnikovii KS1 | 956.2 |
| E. coli HB 101 | 30.3 |

It can be seen from the above results that the vapk gene contained in the recombinant plasmid pSB1 was expressed in E. coli HB 101 and the expressed protease VapK was secreted extracellularly. The protease VapK exhibited optimum activity at pH 10.5 and at 50° C. (FIG. 9). This enzyme showed stability in the entire pH range. However, the stability of the enzyme was influenced slightly by temperature. The protease VapK exerted high resistance to surfactants such as LAS (linear alkylbenzen sulfonate), SDS (sodium dodecyl sulfonate), and AOS (Sodium-α-olefin sulfonate), making it suitable as a laundry detergent. The additional characteristics of the expressed recombinant VapK are shown in Table 2 below.

TABLE 2

Effects of Inhibitors on the activity of the protease VapK

| Inhibitor | Concentration of Inhibitor (mM) | Relative Activity (%) Temperature 4° C. | 20° C. |
|---|---|---|---|
| Metal chelating agent, EDTA | 100 | 86 | 100 |
| Serine protease inhibitor, PMSF | 1 | 6 | 13 |
| Reducing agent, L-cysteine | 1 | 99 | 100 |
| Calcium chelating agent, EGTA | 1 | 100 | 100 |

EDTA: ethylenediamine tetraacetic acid,
PMSF: phenylmethanesulfonyl fluoride,
EGTA: ethyleneglycol-bis(β-aminoethyl ether)N,N,N',N'-tetraacetic acid.
*The enzyme solution was previously reacted with each reagent at the given temperature for 20 minutes.

The results indicated that the enzymatic activity of the protease VapK was inhibited only by PMSF, the serine protease inhibitor. Thus, the protease VapK is a serine protease. In addition, the enzymatic activity of the protease VapK at the temperature 4° C. was nearly identical with that at 20° C. That is, the enzyme VapK showed high activity at low temperature. Accordingly, the protease VapK is an advance over proteases used to date which are active only at high temperature.

In addition, the resistance of the protease VapK to various surfactants was tested. The enzyme sample was appropriately diluted in distilled water. The diluted solution was mixed with each surfactant in the same ratio. The mixture was reacted at 25° C. for 25 minutes. A substrate solution of 5 mM N-succinyl-ala-ala-pro-phe-p-nitroanilide in 1 M tris-HCl, pH 9.0 was added to the reaction mixture in the ratio of 1 to 10. The reaction mixture was reacted at 25° C. for 30 minutes. The optical density of the reaction mixture was measured at 410 nm to determine the enzymatic activity of the protease VapK. The results are shown in Table 3 below.

TABLE 3

| Surfactant | Concentration (ppm) | Relative Residual Activity[a] (%) |
|---|---|---|
| SDS[b] | 1000 | >100 |
|  | 1500 | <70 |
| AOS[c] | 10000 | >100 |
|  | 15000 | >70 |
| Polyoxyethylene Alkylether[d] (EO = 15 mol) | 30000 | >100 |

[a]Value relative to the activity of the enzyme measured in the absence of surfactant
[b]SDS: sodium dodecyl sulfate (anionic surfactant)
[c]AOS: Sodium-α-olefin sulfonate (anionic surfactant)
[d]Nonionic surfactant.

The above results demonstrate that the protease VapK is very stable to anionic surfactants such as SDS and AOS and to nonionic surfactants such as polyoxyethylene alkylether. Under general washing conditions, the amount of surfactant is no more than 1,000 ppm. Therefore, it is believed that the protease VapK remains stable to surfactants during washing.

Example 5

Transformation and Expression of the Recombinant Plasmid pSBCm to V. metschnikovii KS1

Figure 2:
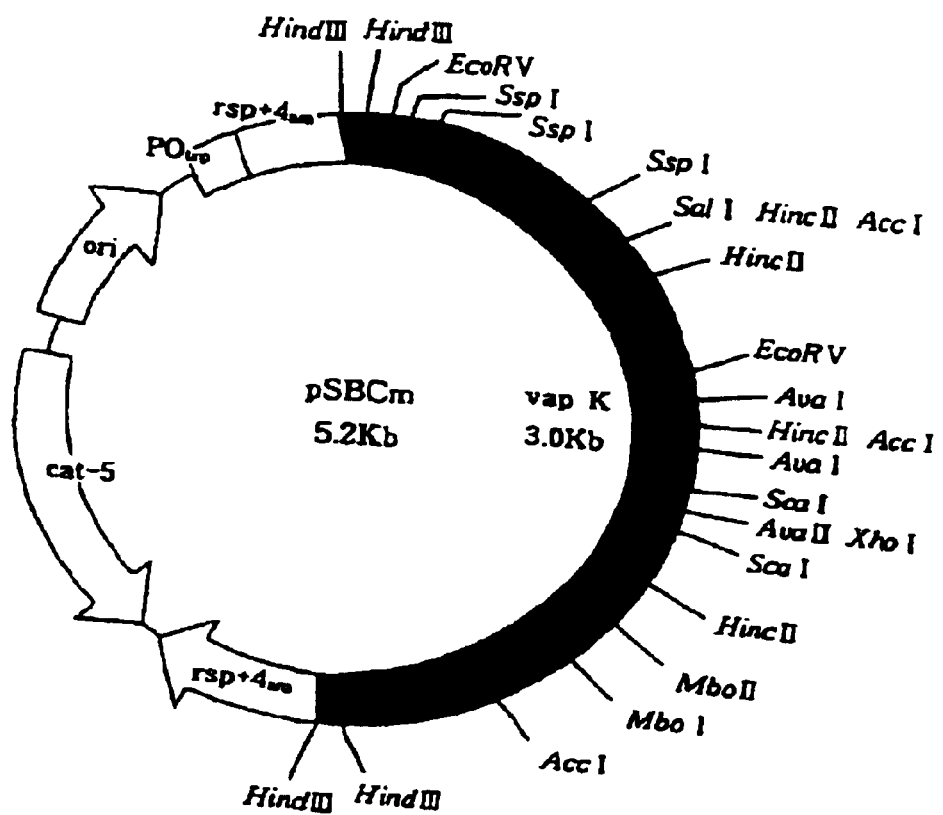
FIG. 2 shows the restriction map of the recombinant plasmid pSBCm of the present invention.
Figure 3:
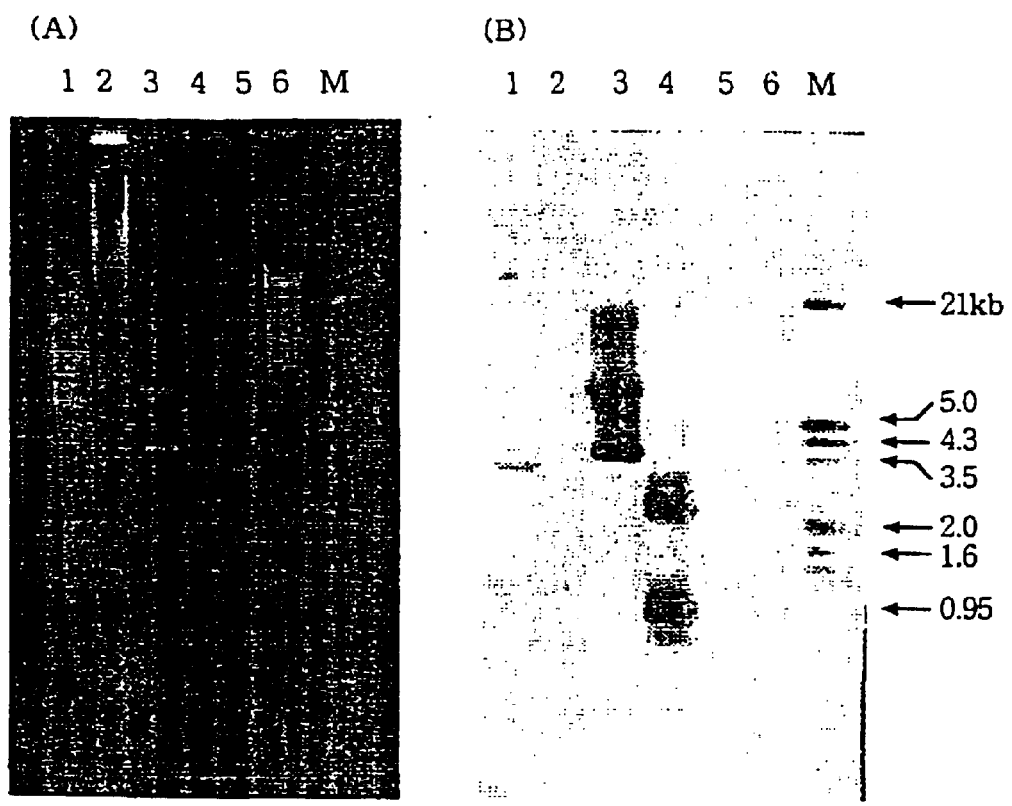
FIG. 3 shows the results of the Southern blotting of the vapk gene.

The V. metschnikovii KS1 was transformed with the recombinant plasmid pSBCm (FIG. 2). Vibrio strains secrete large amount of DNase extracellularly or within the periplasmic space. Furthermore, when the strains are shocked by high temperature, they easily die, even though the DNase is inhibited. Thus, the transformation could not be easily achieved by a conventional heat-shock method. Instead, the transformation was performed by electroporation under the following conditions:
(1) Effect of the Capacitance
The transformation efficiency was tested by varifying the capacitance in the range of 1 $\mu$F to 50 $\mu$F. The survival rate was 96% at 1 $\mu$F and 9% at 50 $\mu$F. The survival rate decreased as the capacitance increased. The transformation efficiency was highest at 10 $\mu$F.
(2) Effect of the Electric Field Strength
The transformation efficiency was tested by varifying the electric field strength in the range of 5 kV/cm to 10 kV/cm while fixing the capacitance at 10 $\mu$F. As a result, the highest transformation efficiency was obtained at 7.5 kV/cm.
(3) Effect of the DNA Concentration
The transformation efficiency was tested by varifying the DNA concentration in the range of 10 ng to 5 $\mu$g while fixing 10 $\mu$F of capacitance and 10 kV/cm of electric field strength. As a result, the transformation efficiency increased in proportion to the DNA concentration. In addition, the enzyme activity of the transformed V. metschnikovii KS1 (pSBCm) was tested. As shown in Table 4 below, the activity of the transformed V. metschnikovii KS1 (pSBCm) was twice as high as that of the host strain V. metschnikovii KS 1.

TABLE 4

| Microorganism | Activity (unit/ml) |
|---|---|
| E. coli HB 101 | — |
| V. metschnikovii KS1 | 900 |
| V. metschnikovii KS1 (pSBCm) | 1500 |

Deposition of Microorganisms and Recombinant Plasmids of the Present Invention

The strain *V. metschnikovii* KS1 of the present invention was deposited with the Korean Culture Center of Microorganisms, Seoul, Korea, on Dec. 15, 1998, as Accession No. KCCM-10141.

Also, the stain *E. coli* Top10F' containing the recombinant vector pSBCm of the present invention was deposited with the Korean Culture Center of Microorganisms on Dec. 15, 1998, as Accession No. KCCM-10142.

---

What is claimed is:

1. An isolated alkaline protease gene comprising the nucleotide sequence of SEQ ID NO:2:

```
agcttctaat acgactcact atagggaaag ctttgctttc      40
ggttttttct gccgcttgac agatatttat gcgattcata      80
atggataaat aatcattata aatcgccatg atgtaaatca     120
agtagactaa aaaacgtaca gttttttta cttaatagtc      160
tatcaatatc attaatttaa ccaataggta acaattcagt     200
aaataaaagc aaacacattc acccagctaa taatagcttt     240
attaataaac tataaaactg gcgaatggct gccgttgtaa     280
tgatccttga tgagtggtat ttgccactaa cattttacaa     320
ggataaaaaa atgttgaaga aaaatgtcaa ccgtacagta     360
ctggctgggt tattgttgcc aacttcaatc tcactggcaa     400
tagcatctca gcttaaggat caagaagtac cgagttttac     440
cccctctgtt gctgttgaaa atcatcaaac agaacaacgc     480
tattttgtta cctacgtgcc tggggcaacc agcggaccaa     520
tgcggatgag tcaaaacggc ttaacagaaa cagatttctc     560
tctgcaaaaa gccgccgata tattaagtac tcagcaagta     600
acggtcatca atcacctcga gtcattacat acttcagtgg     640
ttagagtgac gccaactcaa gccaagcaac tgctcgataa     680
tgctgatgtg gcgatgatcg aagtcgaccc aatacgctat     720
ttattcgatg ctgagattga gccttacgca aacagaccc     760
catacggaat ccgtatggta caagccgatc aactctctga     800
cgttatgcg gctaatcgta aactttgcgt catcgactcg     840
ggatatcttc gcaaccatgt tgatctaccg agcgctggag     880
tcacaggcag cactttctct ggccatggtt catggttcac     920
tgatggcaat ggtcatggaa ctcacgttgc agggacaatt     960
gtcgcactgg ataataatgt cggagttgtt ggggttctac    1000
cgtctggctt agtcggccta cacaacgtaa aaatctttaa    1040
cgattccggt gtctggactc gcgcttcgga tttgattcaa    1080
gctatccaat cttgtcaaag tgcaggcagt catgtggtaa    1120
atatgagttt aggtggtagc caaggcagtg taaccgaaca    1160
aaagccaatg cgtaactttt accaacaagg gatgctctta    1200
gttgcagcag caggtaactc aggaaacagc ggcttctcat    1240
acccggcgtc ttatgatgca gtggtctcag ttgcggcggt    1280
taactcaagt ggtaatgtgg ctaacttctc acagttcaat    1320
tcacaagttg aactctcggc accaggagtt ggggtactat    1360
caaccggtaa taatggcggc tacttaagct atagcggaac    1400
ctcaatggct tcacctcacg ttgcaggtgt cgcagcgctg    1440
gtttggagtc actttccaca atgtcgacca gagcgaatcc    1480
gtcagtcact cagtcaaacg gctctcgatc gtggtgccgc    1520
aggtagagat aatttttacg gttgggggat agttcaagcg    1560
agacgtgcct ataactggtt atctcgcaat ggctgttaat    1600
ttctaatatt gagaatatga acagggtact gagtaccctg    1640
tttgttattt tccagagaca aatctaaccg tctaaattaa    1680
tttgtttaat caattcttct tgtacacggt ctgcctcaga    1720
taagggaatt tgacaggttc cagcggcatg atgaccgccg    1760
ccaccatatt tgagcattaa cgcaccaaca ttggtttgga    1800
actacgatct ttc                                 1813.
```

2. A recombinant plasmid pSB1 containing the gene of claim 1.

3. A recombinant plasmid pSBCm containing the gene of claim 1.

4. A strain *Vibrio metschnikovii* KS1 transformed with the recombinant plasmid pSBCm of claim 3.

5. A process for producing a protease VapK suitable for a laundry detergent which comprises cultivation of the strain of claim 4 under conditions permitting the expression of protease VapK and purifying the protease VapK from the culture.

* * * * *